US009943226B2

(12) United States Patent
Gunn

(10) Patent No.: US 9,943,226 B2
(45) Date of Patent: Apr. 17, 2018

(54) LENS HOLDER FOR CONTACT VITRECTOMY LENS

(71) Applicant: Novartis AG, Basel (CH)

(72) Inventor: Nicholas Max Gunn, Newport Beach, CA (US)

(73) Assignee: Novartis AG (CH)

( * ) Notice: Subject to any disclaimer, the term of this patent is extended or adjusted under 35 U.S.C. 154(b) by 134 days.

(21) Appl. No.: 14/925,282

(22) Filed: Oct. 28, 2015

(65) Prior Publication Data
US 2017/0119249 A1    May 4, 2017

(51) Int. Cl.
| | | |
|---|---|---|
| *A61B 3/00* | (2006.01) | |
| *A61B 3/125* | (2006.01) | |
| *A61F 9/007* | (2006.01) | |
| *A61F 9/009* | (2006.01) | |

(52) U.S. Cl.
CPC ............. *A61B 3/125* (2013.01); *A61F 9/009* (2013.01); *A61F 9/00736* (2013.01)

(58) Field of Classification Search
CPC .. A61F 9/00736; A61F 9/00825; A61F 9/009; A61F 9/0026; A61B 3/125; A61B 3/16; A61B 3/117; A61B 3/12; B65D 75/22; G02B 7/023; G02B 7/028
USPC ......... 351/219, 159.02, 246, 159.37, 159.71, 351/205, 206, 243, 245; 359/642, 708, 359/808, 811; 600/401; 606/1, 4, 5, 7, 606/10, 17; 623/4.1, 6.43
See application file for complete search history.

(56) References Cited

U.S. PATENT DOCUMENTS

| | | | | |
|---|---|---|---|---|
| 4,913,545 | A  * | 4/1990 | Volk ........................ | A61B 3/12 351/205 |
| 6,019,472 | A  * | 2/2000 | Koester .................. | A61B 3/125 351/219 |
| 6,120,147 | A  * | 9/2000 | Vijfvinkel .............. | A61B 3/125 351/159.02 |
| 2004/0036839 | A1 | 2/2004 | Fischer et al. | |
| 2011/0319873 | A1* | 12/2011 | Raksi ..................... | A61F 9/009 606/1 |

OTHER PUBLICATIONS

International Searching Authority, International Search Report and Written Opinion, PCT/IB2016/053577, dated Aug. 10, 2016, 16 pages.

* cited by examiner

*Primary Examiner* — Mustak Choudhury
(74) *Attorney, Agent, or Firm* — Kenneth D. Bassinger

(57) ABSTRACT

A lens holder for holding a vitrectomy lens during a surgical procedure may include a support ring sized and shaped to receive a portion of the vitrectomy lens to provide visualization of a surgical site in an eye of the patient. The support ring may be configured to rest upon the eye of the patient during a surgical treatment procedure performed on the eye. The lens holder may also include a transparent, flexible membrane disposed along a bottom plane of the support ring and configured to conform to a surface feature on the eye. It may also include an overflow trough to control contact of a wetting agent with the eye.

12 Claims, 4 Drawing Sheets

LENS HOLDER FOR CONTACT VITRECTOMY LENS

TECHNICAL FIELD

This disclosure is directed to a lens holder for a contact vitrectomy lens. More particularly, this disclosure is directed to a lens holder that may be positioned and maintained on an eye during a surgical procedure.

BACKGROUND

When performing vitreoretinal surgeries, surgeons use surgical microscopes to perceive tissue in the eye. In some cases, the surgical microscopes are aligned with a contact lens placed directly on the eye. Viscoelastic is often used between the cornea and the contact lens to eliminate any air gap between the two that would otherwise be present due to imperfect matching of the lens curvature to the cornea. The viscoelastic may have a similar refractive index as the lens and cornea to prevent reflections from occurring at their surfaces however the viscoelastic also acts as a lubricant and the lens may easily slide from atop the cornea due to gravity.

One conventional approach for reducing movement of the contact lens due to the force of gravity includes suturing a lens holder to the eye and inserting the lens. Another approach includes attaching the lens to an access cannula implanted in the eye during the surgical procedure. While these approaches reduce the chance of the contact lens displacing along the cornea during the surgical procedure, these approaches also eliminate the opportunity to adjust the lens during the surgical procedure.

Another conventional approach for reducing movement of the contact lens includes using an assistant to manually hold the lens in place during the surgery. This type of approach however is cumbersome and the assistant must have very steady hands for good results.

The present disclosure is directed to systems and methods holding a lens to an eye during a vitreoretinal surgical procedure.

SUMMARY

According to an exemplary aspect, the present disclosure is directed to a lens holder for holding a vitrectomy lens during a surgical procedure. The lens holder may include a support ring sized and shaped to receive a portion of the vitrectomy lens to provide visualization of a surgical site in an eye of the patient. The support ring may be configured to rest upon the eye of the patient during a surgical treatment procedure performed on the eye. The lens holder may also include a transparent, flexible membrane disposed along a bottom plane of the support ring and configured to conform to a surface feature on the eye.

In some aspects, the support ring may include an interior surface, an exterior surface, and a perforation extending through a side of the support ring from the interior surface to the exterior surface. The perforation may include a plurality of perforations equally spaced along the support ring. In some aspects, the lens holder may include an overflow wall adjacent the support ring. The overflow wall may be supported by a lower edge of the support ring. The support ring may include an interior surface and an exterior surface. The overflow wall may form an overflow trough about the exterior surface of the support ring. The overflow wall may include a lower edge connected to a lower edge of the support ring. The overflow trough may be arranged to minimize loss of wetting agent due to overflow/spillage so that additional wetting agent does not need to be reapplied when the lens is positioned or repositioned. The overflow wall may include an interior surface facing the support ring. The interior surface may extend at an oblique angle or a curve relative to the support ring. The transparent, flexible membrane may be configured to separate a wetting agent in the support ring from the eye.

According to another exemplary aspect, the present disclosure is directed to a lens holder with a support ring that may have an inner surface and an outer surface, may have a transparent, flexible membrane disposed along a bottom plane of the support ring that is configured to conform to a surface feature on the eye, and may have a trough disposed outside the outer surface of the support ring. The trough may be configured to inhibit fluid flow from the support ring to the eye.

In some aspects, the support ring may include an inner surface, an outer surface, and a perforation extending through a side of the support ring from the inner surface to the outer surface. The perforation may be one or more perforations equally spaced along the support ring. The overflow wall may be supported by a lower edge of the support ring. In some aspects, an overflow wall may extend about the support ring. The overflow wall may form the overflow trough. The overflow wall may include an interior surface facing the support ring. The interior surface may extend at an oblique angle or curve relative to the support ring.

According to another exemplary aspect, the present disclosure is directed to methods of using a lens system to perform a surgical procedure on an eye. The method may include introducing a wetting agent into a support ring of a lens holder and introducing a vitrectomy lens into the support ring so that an overflow portion of the wetting agent flows out of the support ring. In some implementations, it may include capturing the overflow portion of the wetting agent to inhibit the wetting agent from coming in contact with a surface of the eye.

In some aspects, introducing a wetting agent into a support ring may include introducing the wetting agent onto a transparent flexible membrane. The method also may include placing the lens system directly on the eye so that the flexible membrane conforms to a surface of the eye. In some aspects, the method may include viewing a surgical site through the vitrectomy lens and the wetting agent while performing a surgical procedure.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

Figure 1:
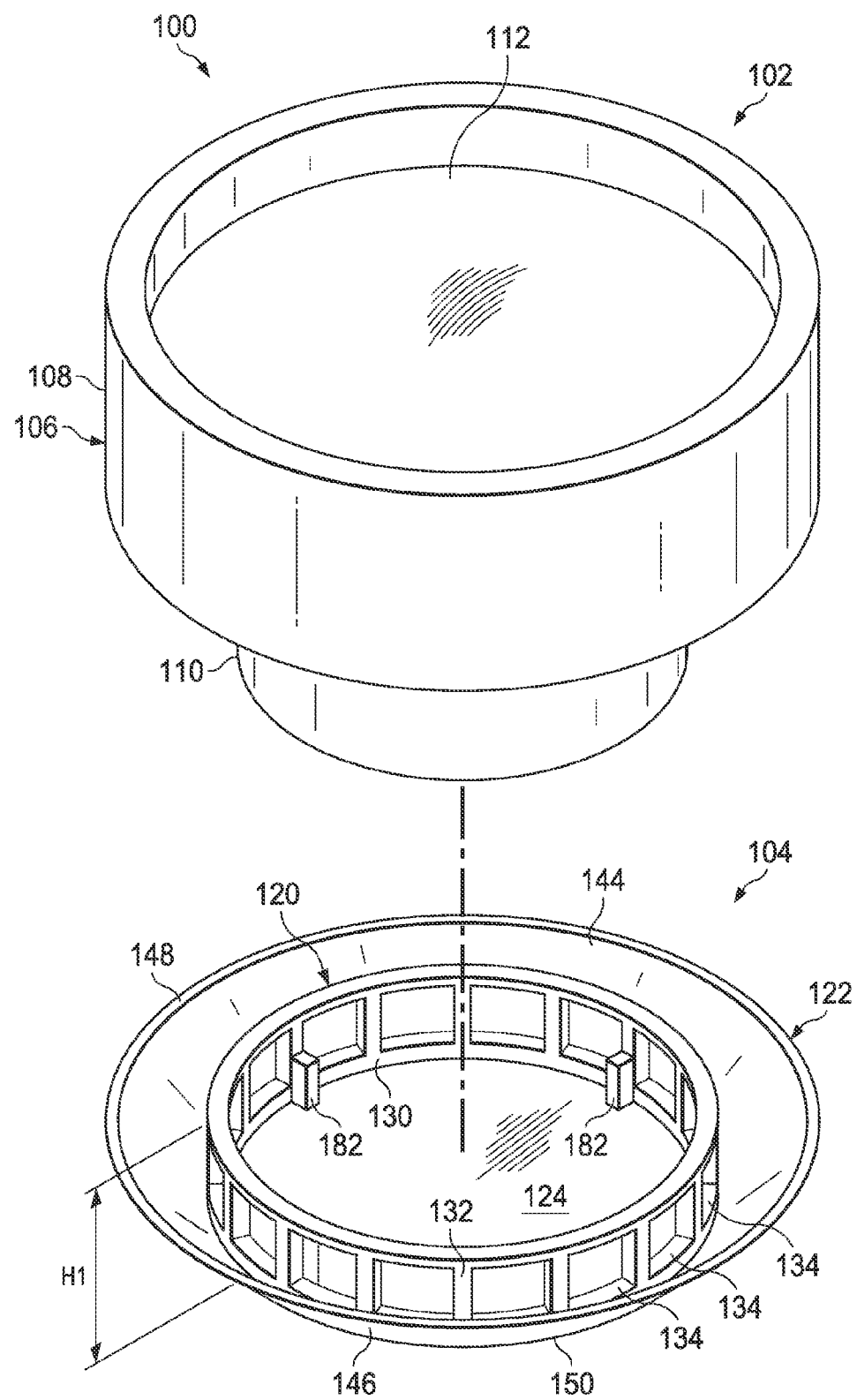
FIG. 1 is an illustration of an exemplary lens system according to an exemplary aspect.

These Figures will be better understood by reference to the following Detailed Description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In addition, this disclosure describes some elements or features in detail with respect to one or more implementations or Figures, when those same elements or features appear in subsequent Figures, without such a high level of detail. It is fully contemplated that the features, components, and/or steps described with respect to one or more implementations or Figures may be combined with the features, components, and/or steps described with respect to other implementations or Figures of the present disclosure. For simplicity, in some instances the same or similar reference numbers are used throughout the drawings to refer to the same or like parts.

The present disclosure relates generally to a lens holder for vitreoretinal surgery. The lens holder is configured to have a higher coefficient of friction than conventional lens holders because it includes a transparent membrane that separates a wetting agent, such as viscoelastic, from coming into direct contact with the cornea. The wetting agent may have a similar refractive index as the lens and cornea to prevent reflections from occurring at their surfaces. Since the wetting agent may include lubricous properties, separating it from the cornea may result in a more stable positioning of the lens. Instead of disposing the wetting agent between the lens and the cornea, the wetting agent is disposed between the lens and the transparent membrane. The transparent membrane may have a similar refractive index as the lens and cornea and wetting agent to prevent reflections from occurring at their surfaces. In some exemplary aspects, the lens holder also includes an overflow trough for capturing excess wetting agent that may be disposed between the lens and the transparent membrane. Because the membrane is in contact with the eye rather than the wetting agent, the holding friction is much higher than in conventional systems and the lens may stay in position without slippage. Furthermore the user can easily reposition the lens by lifting it and placing it in a desired position. The wetting agent flows in and out of the overflow trough through perforations to continuously maintain the wetting agent in place without the need for the surgeon to reapply it during lens repositioning.

FIG. 1 illustrates a lens system 100 including a vitrectomy lens 102 and a lens holder 104. The lens system 100 may be used during an ocular surgery to enable a user such as a surgeon to be able to view a surgical site. In some implementations, the lens system 100 is disposed upon and placed in contact with an eye undergoing a surgical procedure.

Here, the vitrectomy lens 102 is shown separate from but disposed above the lens holder 104. The lens holder 104 may be used with any of a large variety of vitrectomy lenses. Accordingly, a surgeon may select any desired vitrectomy lens and it may cooperate with the lens holder 104 to provide desired visualization capability. In some implementations, the lens holder 104 is compatible with specific vitrectomy lenses or family of lenses. In some implementations, the lens holder 104 may be one of a set of similarly shaped lens holders, each designed to be used with a specific vitrectomy lens or family of lenses.

The vitrectomy lens 102 may include a body 106 divided into a wide diameter lens holding portion 108 and a smaller diameter lens holding portion 110. The wide diameter lens holding portion 108 may include a lens 112, and the smaller diameter lens holding portion 110 may include an additional lens that is not shown in this embodiment. Light may pass through open ends of the body 106, and through the lenses. The lenses may cooperate together to magnify a surgical site for viewing by a user.

The lens holder 104 may be sized and arranged to receive a portion of the body 106 of the vitrectomy lens 102. In this implementation, the lens holder 104 is sized and arranged to receive the smaller diameter lens holding portion 110. The lens holder 104 is sized and shaped to separate the vitrectomy lens 102 from direct contact with an eye. In this implementation, the lens holder 104 includes a main body, referred to herein as a support ring 120, an overflow wall 122, and a flexible membrane 124.

Figure 2:
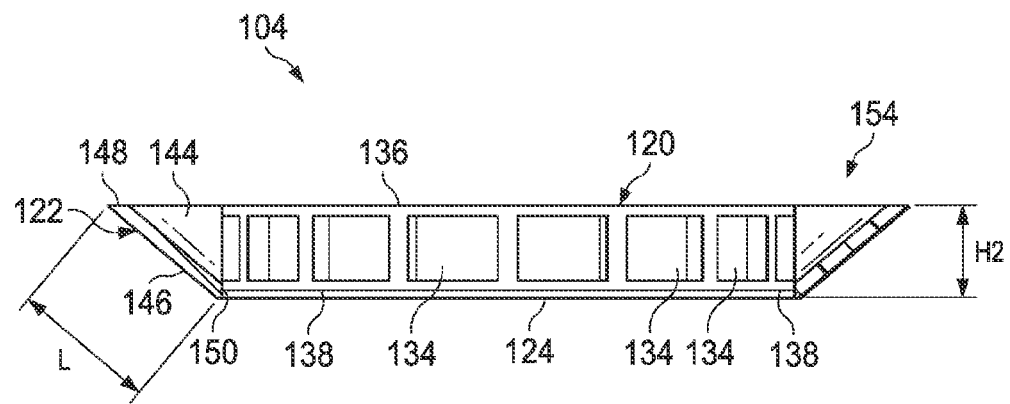
FIG. 2 is an illustration of a plan view of an exemplary lens holder according to an exemplary aspect.
Figure 3:
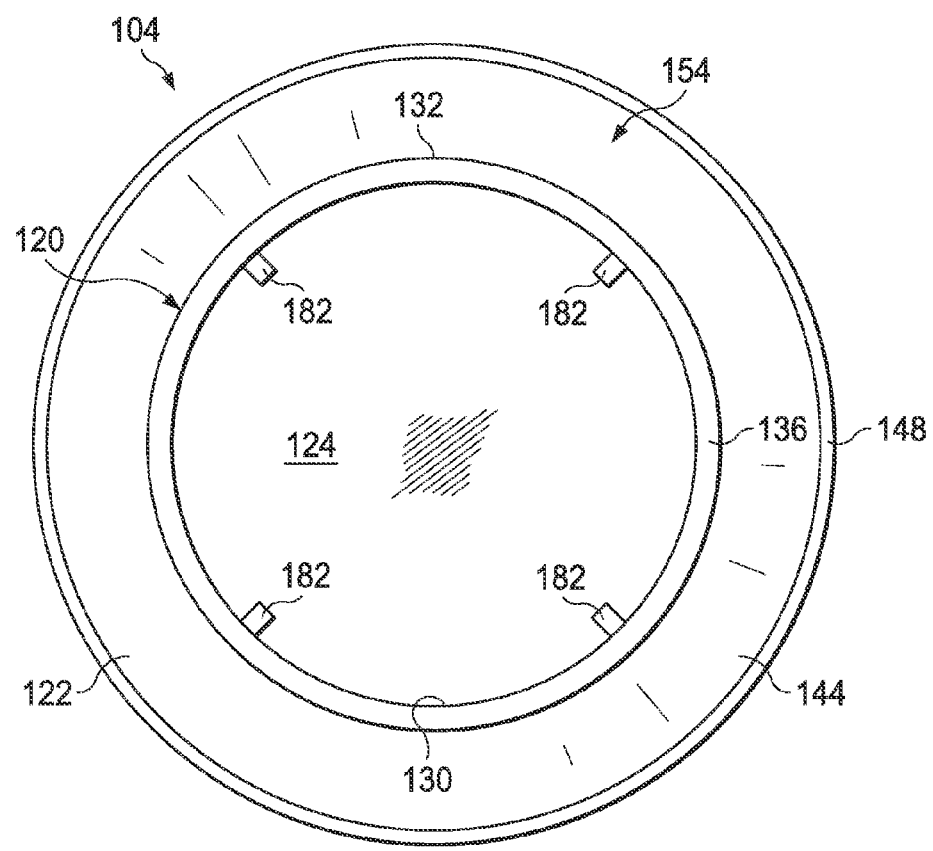
FIG. 3 is an illustration of a top view of the exemplary lens holder according to an exemplary aspect.

FIGS. 2 and 3 illustrate a side view and a top view of the lens holder 104. Referring to FIGS. 1, 2, and 3, the support ring 120 includes an inner surface 130 and an outer surface and 132. The support ring 120 has a diameter sized slightly larger than the diameter of the smaller diameter lens holding portion 110 of the vitrectomy lens 102 of FIG. 1. The support ring 120 is configured to receive the smaller diameter lens holding portion 110 in a manner that permits insertion and removal. In some implementations, the support ring 120 has a diameter within the range of about 0.1 to 1 inches. Smaller and larger diameters are also contemplated. The support ring 120 has an upper edge 136 and a lower edge 138, best seen in FIG. 2. The lower edge 138 may form a bottom portion of the lens holder 104. The support ring 120 may have a height H1 measured from the upper edge 136 to the lower edge 138 within a range of about 0.05 to 0.2 inch. Smaller and larger heights are also contemplated. In this exemplary embodiment, the support ring 120 is cylindrical and includes a series of perforations 134 formed therein. The perforations 134 extend from the inner surface 130 to the outer surface 132. These perforations 134 are sized and arranged to allow a wetting agent, such as viscoelastic, to flow therethrough. In the embodiment shown, the perforations 134 are rectangular shaped. However the perforations 134 may be any shape suitable for passing a wetting agent, including viscoelastic, therethrough. For example, the perforations may be round, oval, square, or other geometric shape. In the implementation shown, the upper edge 136 is a closed circle, while in other implementations, the upper edge may include gaps or breaks.

In the exemplary implementation shown, the overflow wall 122 extends from the lower edge 138 of the support ring 120 in an upward direction tapering outwardly from the support ring 120. Thus, in this exemplary implementation, the overflow wall 122 is in the shape of a frustum. The overflow wall 122 includes an interior surface 144, an exterior surface 146, and upper edge 148, and a lower edge 150.

In this implementation, the overflow wall 122 has a length L and a height H2, with the length L being greater than the height H2. Here, the upper edge 148 of the overflow wall 122 is at approximately the same height H2 as the height H1 of the upper edge 136 of the support ring 120. In other implementations, the overflow wall 122 may have a greater or lower height H2 than the height H1 of the support ring 120. For example, the height H2 may range from about 0.05-0.5 inches in some embodiments. Other heights and ranges are contemplated.

The overflow wall 122 may extend at an angle relative to the support ring 120. In the implementation shown, the overflow wall 122 extends at about a 40° angle as measured from a plane including the lower edge 138 of the support ring 120. Other implementations include an overflow wall 122 at a different angle. For example, in some implementations the overflow wall 122 is formed at an angle from a plane including the lower edge 138 within a range of about 5° to 70°. Some overflow walls are angled within a range of about 20° to 50°. Still other angles are contemplated. The lower edge 150 of the overflow wall 122 may extend from the lower edge 138 of the support ring 120. In some implementations, only the interior surface 144 of the overflow wall 122 is angled. In some implementations, the interior surface 144 and exterior surface 146 of the overflow wall 122 are at non-similar angles.

The area between the interior surface 144 of the overflow wall 122 and the outer surface 132 of the support ring 120 forms an overflow trough 154. The overflow trough 154 is arranged to capture the wetting agent, such as the viscoelastic, that may be disposed between the vitrectomy lens 102 and the lens holder 104. The overflow trough 154 may therefore act to reduce or minimize the amount of wetting agent in contact with a patient's cornea or that drips or otherwise escapes from its intended location between the vitrectomy lens 102 and the lens holder 104. Since the interior surface 144 is disposed at an angle, the wetting agent may be inclined to flow through the perforations 134 and into the support ring 120.

The flexible membrane 124 is disposed at a very bottom portion of the lens holder 104 and spans the opening defined by the support ring 120. The membrane 124 may be located in a position to contact and lie upon the cornea of a patient when the lens holder 104 is in use. Because the flexible membrane 124 may stretch, bend, flex, or otherwise deform its shape, the flexible membrane may conform to the shape of the cornea, so that air gaps or other features that may affect visualization are minimized. The flexible membrane 124 may be clear so that visualization through the vitrectomy lens 102 is maximized. The flexible membrane 124 may be made from a hydrogel material, such as silicone hydrogel, polyvinyl alcohol hydrogel, polyethylene glycol based hydrogel, or other hydrogels. The material of flexible membrane 124 may have high water content and/or high water permeability so that the cornea of the eye remains moist or well-wetted during the surgical procedure. The material may also have high oxygen permeability. The material may be micro or macro porous to improve water or oxygen permeability. The flexible membrane 124 may be made from other clear materials such as polyvinyl chloride, low density polyethylene, or others. The flexible membrane 124 may have a high degree of elasticity so that it can conform to the shape of the cornea. The thickness of the flexible membrane 124 may be within the range of 0.001 inches to 0.1 inches. Thinner and thicker thicknesses are also contemplated. In some embodiments, the flexible membrane 124 has a coefficient of friction that is greater than a vitrectomy lens placed directly on a wetting agent that is directly on the cornea. Accordingly, the lens holder 104 is less inclined to move across the cornea than a vitrectomy lens placed directly on the eye.

While the lens holder 104 has been described as having multiple elements that together make up the lens holder 104, in some implementations the support ring 120 and the overflow wall 122 are a single monolithic component. In some implementations the support ring 120 and the overflow wall 122 are formed of a material that may include, for example, plastic, polymer, metal, glass, or other materials. In other implementations, the support ring 120 and the overflow wall 122 are formed as separate components and assembled together to form the lens holder 104. The flexible membrane 124 may be secured to the lower edge 138 of the support ring 120. In some implementations, the flexible membrane 124 is sealed to the lower edge 138 of the support ring 120 in a manner that prevents fluids, including wetting agents, from passing out of the support ring 120.

In some implementations, the lens holder 104 is a disposable lens holder. It may be formed of an inexpensive polymer material and may be discarded after each use. In some implementations, the lens holder 104 may be integrated into a disposable vitrectomy lens and the entire assembly disposed of after the surgical procedure. In other implementations, the lens holder 104 may be reusable. In such implementations, it may be autoclavable for re-sterilization.

Figure 5A:
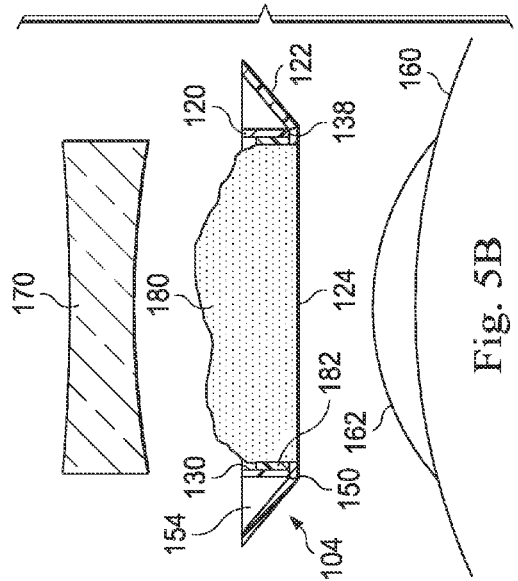
FIGS. 5A through 5D illustrate exemplary steps of a method of using a lens system to perform a surgical procedure according to exemplary aspects.

A single lens 170 in FIG. 5A is disposed above the lens holder 104. In this Figure, the lens 170 represents the vitrectomy lens 102. Although only the single lens 170 is shown, it should be understood that the single lens 170 is only one lens of the vitrectomy lens 102 and is shown in this manner for simplicity. The lens 170 is shown in cross-section, and its two concave surfaces form the lens. In other implementations, other lenses may be used.

Figure 4:
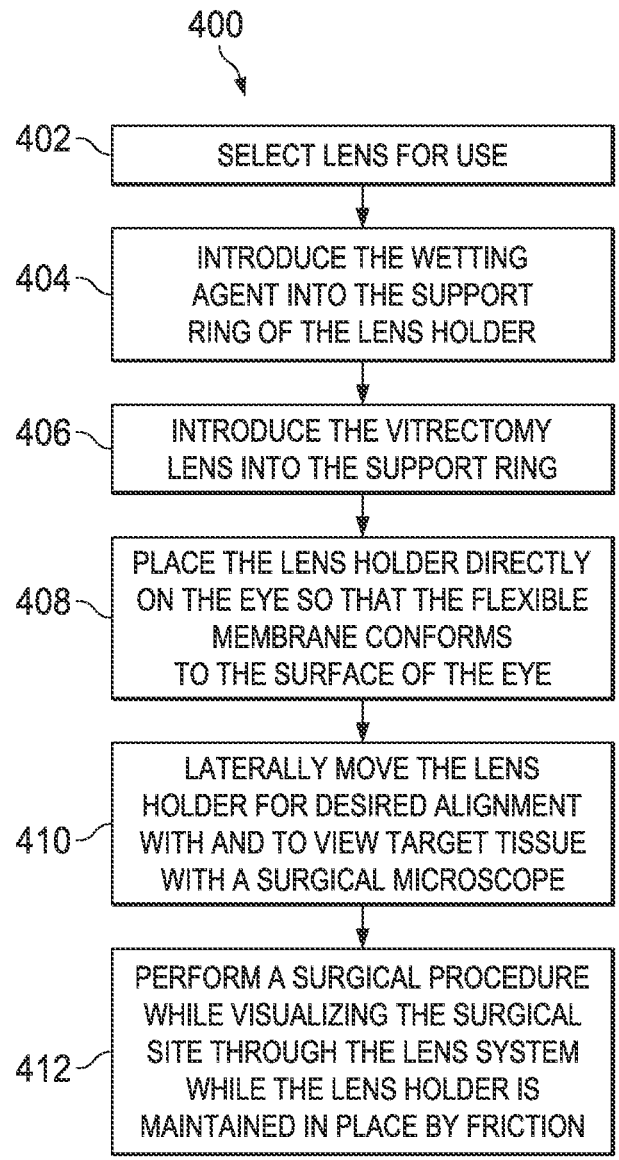
FIG. 4 shows a flow chart of an example method of using a lens system to perform a surgical procedure according to an exemplary aspect.

An exemplary method of using the support ring 120 in a surgical application is described with reference to FIGS. 4 and 5A through 5D. FIG. 4 describes an exemplary method 400 for using the lens holder 104. FIGS. 5A through 5D illustrate portions of the exemplary method 400 and show cross-sectional images of the lens holder 104 to hold a vitrectomy lens 170 against a patient's eye.

The method begins at 402 by a user selecting a vitrectomy lens, such as the vitrectomy lens 102, for use during the surgical application. The vitrectomy lens may be any conventional lens including, for example only, a biconcave lens, a magnifying lens, a wide-field the lens, a prism lens, an inverted image lens, or other lens. In some implementations, the user may select a single vitrectomy lens or a plurality of lenses. In some instances, the user may select a single vitrectomy lens and combine it with an additional bite vitrectomy lens within a lens holding body, such as the lens holding body 106.

FIG. 5A shows the lens holder 104 and a vitrectomy lens 170 in cross-section above a cornea 162 of the patient's eye 160. Here, the vitrectomy lens 170 may be a lens forming a part of the fight vitrectomy lens 102 of FIG. 1. In some implementations, the vitrectomy lens 170 may be a lens disposed within the smaller diameter lens holding portion 110 of the vitrectomy lens 102. FIG. 5A shows the lens holder 104 disposed immediately above the cornea 162. Since the lens holder 104 is shown in cross-section, the flexible membrane 124 may be seen relative to the support ring 120 and the overflow wall 122. Here, the flexible membrane 124 is disposed adjacent to or flush with the lower edge 138 of the inner surface 130 so that it forms the bottom plane of the lens holder. Accordingly, when the lens holder 104 is placed on the eye 160, the flexible membrane 124 is disposed in contact with the cornea 162 of the eye 160. As described further below, the membrane 124 is located in a position to contact and conform to the shape of the cornea 162 in a manner that eliminates any gaps or bubbles.

Figure 5B:
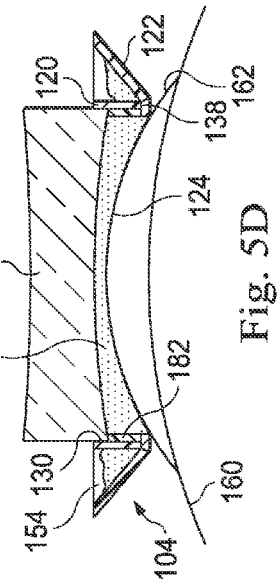

Returning to FIG. 4, at 404, a wetting agent 180 is introduced into the support ring 120 of the lens holder 104 atop the flexible membrane. FIG. 5B shows the lens holder 104 after having been filled with a wetting agent 180. The wetting agent 180 may include any conventional material used in surgical applications with vitrectomy lenses to fill gaps and reduce bubbles that may impact visualization through the lenses. In some implementations, the wetting agent is a viscoelastic material. Other wetting agents may also be utilized. As can be seen in FIG. 5B, the wetting agent 180 is disposed directly on the flexible membrane 124 within the support ring 120. Here, the wetting agent 180 is not in contact with the cornea 162.

Figure 5C:
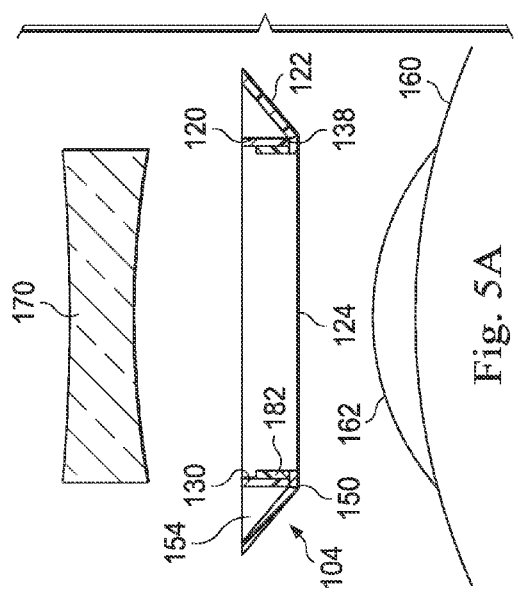

At 406 in FIG. 4, the vitrectomy lens is introduced into the support ring 120. FIG. 5C shows the lens 170 after being introduced into the lens holder 104. The lens 170 may be introduced into the support ring 120 so that it becomes embedded in the wetting agent 180. In some implementations, the vitrectomy lens snaps into a top portion of the support ring 120. This also compresses the wetting agent 180 against the flexible membrane 124. In some implementations, the membrane may flexed, distorted, or otherwise displaced when the wetting agent 180 is compressed between the lens 170 and flexible membrane 124. In this position, the wetting agent is continuous between the flexible membrane 124 and a bottom surface of the vitrectomy lens. As such, air or gaps between the wetting agent 180 and the lens 170 or between the wetting agent and flexible membrane 124 may be minimized or prevented. As the lens 170 is introduced into the support ring 120, excess wetting agent 180 may flow through the perforations 134 (FIG. 2) and into the overflow trough 154. The overflow trough 154 may prevent the wetting agent overflow from coming into contact with the cornea 162 or being lost from the lens holder. In some embodiments, the support ring 120 may include hard stops 182 formed as shoulders on the inner surface 130 that limit the distance that the lens 170 may enter the support ring 120. Here, the lens 170 abuts the hard stops 182.

Figure 5D:
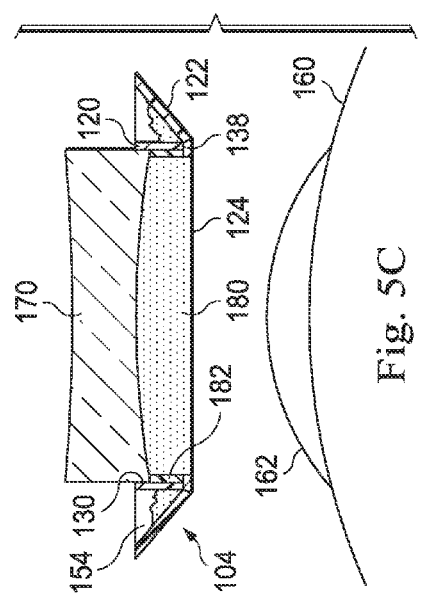

With the lens 170 disposed within the support ring 120 the lens system, including both the lens 170 and the support ring 120, may be introduced to the eye 160. At 408 in FIG. 4, the lens holder 104 may be placed directly on the eye so that the flexible membrane 124 conforms to the surface of the cornea 162 of the eye 160. FIG. 5D shows the lens system in contact with the cornea 162 of the eye 160. Since the flexible membrane 124 is configured and arranged to conform to the shape of the cornea, the flexible membrane 124 matches and aligns with the cornea shape. As such, during the process of placing the lens system on the cornea 162, the flexible membrane displaces into an interior region of the support ring 120. When the flexible membrane bows upwardly to match the curvature of the cornea, additional wetting agent 180 may flow out of the perforations 134 and into the overflow trough 154. Again, the overflow trough 154 captures the wetting agent 180 and helps keep the wetting agent from becoming disposed on the cornea 162 or lost as waste. In some methods, the eye 160 may be moistened with a wetting agent, including drops or viscoelastic prior to placing the lens holder 104 on the eye 160.

At 410 in FIG. 4, a user may latterly move the lens holder for a desired alignment with and to view target tissue with a surgical microscope. Since the lens system, including the vitrectomy lens 170 and the lens holder 104, may be displaced manually independent of the microscope, a user may orient the lens system as desired. For example, a user may slide the lens system across the cornea to a desired position, or the user may lift the lens system off of the cornea and place it in another position on the cornea as desired. When the lens system is moved along the cornea, the flexible membrane 124 may displace so that the flexible membrane maintains direct contact with the cornea 162 or other surface features of the eye. When the lens system is lifted off the cornea, the flexible membrane 124 may displace to the position shown in FIG. 5C. When this occurs, the volume between the vitrectomy lens 170 and the flexible membrane 124 increases. Wetting agent may flow from the overflow trough, through the perforations, and into the support ring 120. Accordingly, even when the lens system is displaced, it may not be necessary to apply additional wetting agent. That is, the wetting agent may flow into and out of the support ring 120 through the perforations 134. When the lens system is placed in a new position, some of the wetting agent may again flow from inside the support ring, through the perforations, into the overflow trough 154. The angled shape of the interior surface 144 of the overflow trough 154 may help prevent spillover of wetting agent from the overflow trough 154 and assist the flow of wetting agent into the perforations and into the support ring 120.

At a step 412, a user may perform a surgical procedure while visualizing the surgical site through the lens system. Here, the lens holder may be maintained in place by friction between the flexible membrane 124 and the surface of the cornea 162 or other part of the eye 160. Because the flexible membrane, rather than the wetting agent, is in contact with the eye, the holding friction is much higher than conventional systems and the lens system may stay in position without slipping. That is, because the wetting agent 180 is not in contact with the cornea 162, the coefficient of friction of the flexible membrane 122 may be maintained at a level sufficient to prevent the lens holder 104 with the vitrectomy lens 102 from sliding on the eye 160 in response to the force of gravity. Accordingly, during a surgical procedure, an extra person may not be required to hold the lens holder 104 in place. Instead, the lens holder 104 may be maintained in place simply by friction between the cornea 162 and the membrane 122. In addition, because the lens system may be movable about an eye during a single surgical procedure, the lens system provides advantages over lens holders that are sutured to an eye of the patient. Here, the wetting agent 180 still performs its purpose of eliminating gaps due to curvature mismatch or imperfections found between the cornea 162 and the lens 170. The flexible membrane 124 may conform to the shape of the cornea 162 so that it to eliminate any gaps or air that may be found between the cornea and the flexible membrane 124. Therefore, a user may be able to obtain good visualization of the interior of the eye 160 through the lens 170, the wetting agent 180, and the cornea 162.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A lens holder for holding a vitrectomy lens during a surgical procedure, comprising:
   a support ring sized and shaped to receive a portion of a vitrectomy lens to provide visualization of a surgical site in an eye of a patient, the support ring being configured to rest upon the eye of the patient during a surgical treatment procedure performed on the eyed the support ring comprising an interior surface, an exterior surface, and a perforation extending through a side of the support ring from the interior surface to the exterior surface;
   a transparent, flexible membrane disposed along a bottom plane of the support ring, and configured to conform to a surface feature on the eye, the transparent, flexible membrane sealed to a lower edge of the support ring;
   an overflow wall adjacent the support ring, the overflow wall comprising a lower edge, the lower edge of the overflow wall coupled to the lower edge of the support ring such that an overflow trough is formed about the exterior surface of the support ring between the exterior surface of the support ring and an interior surface of the overflow wall; and
   wherein the overflow trough is arranged to minimize loss of wetting agent due to overflow/spillage.

2. The lens holder of claim 1, wherein the perforation comprises a plurality of perforations spaced along the support ring.

3. The lens holder of claim 1, wherein the interior surface of the overflow wall is facing the support ring, the interior surface extending at an oblique angle relative to the support ring.

4. The lens holder of claim 1, wherein the transparent, flexible membrane is formed of a hydrogel material.

5. The lens holder of claim 1, wherein the transparent, flexible membrane is configured to separate a wetting agent in the support ring from the eye.

6. A lens holder for holding a vitrectomy lens during a surgical procedure, comprising:
   a support ring sized and shaped to receive a portion of the vitrectomy lens to provide visualization of a surgical site in an eye of a patient, the support ring being configured to rest upon the eye of the patient during a surgical treatment procedure performed on the eye, the support ring having a lower edge, an inner surface and an outer surface;
   a transparent, flexible membrane disposed along a bottom plane of the support ring and sealed to the lower edge, and configured to conform to a surface feature on the eye;
   a trough disposed completely around the outer surface of the support ring and configured to inhibit fluid flow from the support ring to the eye; and
   wherein an overflow wall forming a portion of the trough, the overflow wall coupled to the lower edge of the support ring.

7. The lens holder of claim 6, wherein the support ring comprises an inner surface, an outer surface, and a perforation extending through a side of the support ring from the inner surface to the outer surface.

8. The lens holder of claim 7, wherein the perforation comprises a plurality of perforations spaced along the support ring.

9. The lens holder of claim 6, comprising an overflow wall extending about the support ring, the overflow wall forming the trough.

10. The lens holder of claim 9, wherein the overflow wall includes an interior surface facing the support ring, the interior surface extending at an oblique angle or a curve relative to the support ring.

11. A method of using a lens system to perform a surgical procedure on an eye, comprising:
   placing a wetting agent into a support ring of a lens holder, the lens holder comprising a support ring with an inner surface, an outer surface and a lower edge, a flexible membrane located at the lower edge and sealed to the lower edge, a perforation extending from the inner surface to the outer surface, and a trough disposed around the outer surface;
   placing a vitrectomy lens into the support ring so that an overflow portion of the wetting agent flows out of the support ring and into the trough;
   capturing the overflow portion of the wetting agent in the trough to reduce loss of the wetting agent and maintain overflow of the wetting agent in immediate proximity to the support ring; and
   placing the lens holder directly on the eye so that the flexible membrane conforms to a surface of the eye.

12. The method of claim 11, comprising viewing a surgical site through the vitrectomy lens and the wetting agent while performing a surgical procedure.

* * * * *